United States Patent
Massie et al.

(10) Patent No.: US 6,620,618 B2
(45) Date of Patent: Sep. 16, 2003

(54) COMPLEMENTARY CELL LINE FOR THE GROWTH OF ADENOVIRUS MUTANTS WITH A DELETED PROTEASE GENE

(75) Inventors: Bernard Massie, Laval (CA); Wahiba Oualikene, Montreal (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/820,824

(22) Filed: Mar. 30, 2001

(65) Prior Publication Data

US 2001/0026938 A1 Oct. 4, 2001

Related U.S. Application Data

(62) Division of application No. 09/258,209, filed on Feb. 25, 1999, now Pat. No. 6,291,226.

(51) Int. Cl.⁷ .................................................. C12N 5/10
(52) U.S. Cl. ...................... 435/369; 435/366; 435/69.1; 435/456; 435/457; 435/465
(58) Field of Search ................................ 435/456, 457, 435/465, 369, 366, 69.1

(56) References Cited

U.S. PATENT DOCUMENTS 5,994,134 A * 11/1999 Giroux et al. .............. 435/403

FOREIGN PATENT DOCUMENTS

WO      WO 95/02697      *  1/1995

* cited by examiner

Primary Examiner—Donna C. Wortman
(74) Attorney, Agent, or Firm—J. Wayne Anderson (57) ABSTRACT

An adenovirus vector/packaging cell line system is disclosed, in which the vector replication is blocked by deletion of a single gene, which deletion does not interfere with any other viral functions. The deleted gene is the gene of the adenovirus protease. The protease is expressed in a complementing (packaging) cell line through a regulatable expression cassette which induces no toxic effects in the cells, thus making the generation and propagation of the vector easier and more efficient. As the deleted gene is highly specific of adenovirus, no complementation of the gene in transduced cells is expected, which increases the safety of the new vectors for gene transfer purposes. Also disclosed is a new system of generating recombinant adenovirus vectors by positive selection of recombinants deleted for the endogenous protease gene, which gene is cloned in another region of the adenoviral genome.

29 Claims, 7 Drawing Sheets

SEQUENCE LISTING

<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 1

```
gtcgaccatg gacgagccca cccttct                                          27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 2
ggatccggcg gcagctgttg ttgatgt                                          27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
agatctaaat aatgtactag agacact                                          27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 4
ctcgagttcc accaacactc cagagtg                                          27
```

COMPLEMENTARY CELL LINE FOR THE GROWTH OF ADENOVIRUS MUTANTS WITH A DELETED PROTEASE GENE

This application is a divisional of Applicant's U.S. application Ser. No. 09/258,209 filed Feb. 25, 1999 now U.S. Pat. No. 6,291,226.

FIELD OF THE INVENTION

The present invention relates to gene therapy, in particular to recombinant adenovirus vectors useful for gene transfer and protein production, for applications in gene therapy and functional genomics and vaccination, and to complementing cell lines for the generation and propagation of such vectors. More particularly, the invention relates to adenovirus mutants deleted at least for the gene of the adenovirus protease, to complementing cell lines expressing the protease and to corresponding gene transfer vectors.

BACKGROUND OF THE INVENTION

The term "gene therapy" is usually understood to mean the process in which a gene is introduced into the somatic cells of an individual with the aim of being expressed in the cells, to produce some therapeutic effect. Initially this principle was applied to cases where an additional normal copy of a defective gene was provided to restore the synthesis of a missing protein, such as an enzyme. The concept of gene therapy has since been broadened to include several other approaches. In particular, the transferred gene (transgene) may code for a protein that is not necessarily missing but that may be of therapeutic benefit and difficult to administer exogenously, for example IL-2 or antitumor cytokines. This form of gene therapy aims to enhance in vivo production of potentially therapeutic proteins. This approach is similar to gene vaccination, where the transferred gene is introduced into the cells to express a protein acting as an antigen inducing a protective immune response of the host's immune system. Another form of gene therapy involves transferring into cells non-physiological sequences which have antiviral activity, such as antisense oligonucleotides or sequences. Finally, so-called suicide genes can be transferred into undesirable cells (cancer cells or infected cells), to sensitize them to specific substances. When these substances are administered subsequently, they trigger selective destruction of the targeted cells.

Gene delivery systems which transfer the desired gene into the target cells are based either on physico-chemical or on biological methods. In each case the desired gene can be transferred into cells either in vitro, by extracting cells from an organ and reintroducing the cells transfected in vitro into the same organ or organism, or in vivo, i.e., directly into an appropriate tissue. Known physico-chemical methods of transfection include, for example, gene gun (biolistics), in situ naked DNA injections, complexes of DNA with DEAE-dextran or with nucleic proteins, liposomal DNA preparations, etc. Biological methods, considered to be a more reliable alternative to physico-chemical methods, rely on infectious agents as gene transfer vectors. In this group of methods, viruses have become infectious agents of choice, due to their inherent capability of infecting various cells. The transfer of a foreign gene by a viral vector is known as transduction of the gene.

Several virus classes have been tested for use as gene transfer vectors, including retroviruses (RSV, HMS, MMS, etc.), herpesviruses (e.g., HSV), poxviruses (vaccinia virus), adenoviruses (Ad, mainly derived from type 5 and 2 Ad) and adeno-associated viruses (AAV). Of those, adenovirus-based vectors are presently considered to be among the most promising viral vectors, due to their following properties, some of which are unique to this group of vectors: (i) adenovirus vectors do not require cell proliferation for expression of adenovirus proteins (i.e., are effective even in cells at the resting phase); (ii) adenovirus vectors do not integrate their DNA into the chromosomes of the cell, so their effect is impermanent and is unlikely to interfere with the cell's normal functions; (iii) adenovirus vectors can infect non-dividing or terminally differentiated cells, so they are applicable over a wide range of host cells; (iv) adenovirus vectors show a transducing efficiency of almost 100% in a variety of animal cultured cells and in several organs of various species in vivo; (v) adenovirus vectors usually possess an ability to replicate to high titer, a feature important for the preparation of vector stocks suitable for the achievement of efficient transduction in vivo; (vi) adenovirus vectors can accommodate large inserts of exogenous DNA (have a high cloning capacity); (vii) recombination events are rare for adenovirus vectors; (viii) there are no known associations of human malignancies or other serious health problems with adenovirus infections; (adenovirus type 5 is originally known to cause cold conditions in humans; live adenovirus of that type having the ability to replicate has been safely used as a human vaccine (Top et al.,*J.I.D.*,124,148–154; *J.I.D.*,124,155–160(1971)).

Structurally, adenoviruses are non-enveloped viruses, consisting of an external capsid and an internal core. Over 40 adenovirus subtypes have been isolated from humans and over 50 additional subtypes from other mammals and birds. All adenoviruses are morphologically and structurally similar, even though they differ in some properties. Subtypes of human adenoviruses are designated according to serological response to infection. Of those, serotypes Ad2 and Ad5 have been studied most intensively, and used for gene transfer purposes since the 80s. Genetically, adenovirus is a double-stranded DNA virus with a linear genome of about 36 kb. The genome is classified into early (E1–E4) and late (L1–L5) transcriptional regions (units). This classification is based on two temporal classes of viral proteins expressed during the early (E) and late (L) phases of virus replication, with viral DNA replication separating the two phases.

A viral gene transfer vector is a recombinant virus, usually a virus having a part of its genome deleted and replaced with an expression cassette to be transferred into the host cell. Additionally to a foreign (exogenous) gene, the expression cassette comprises components necessary for a proper expression of the foreign gene. It contains at least a promoter sequence and a polyadenylation signal before and after the gene to be expressed. Other sequences necessary to regulate or enhance the gene expression can be included in the cassette for specific applications.

The deletion of some parts of the viral genome may render the virus replication-incompetent, i.e., unable to multiply in the infected host cells. This highly desirable safety feature of viral vectors prevents the spread of the vector containing the recombinant material to the environment and protects the patient from an unintended viral infection and its pathological consequences. The replication-defective virus requires for its propagation either a complementing cell line (packaging cell line) or the presence of a helper virus, either of which serves to replace (restore in trans) the functions of the deleted part or parts of the viral genome. As it has been shown that the production of recombinant viral vectors free of replication-competent helper virus is difficult to achieve, the use of packaging cell lines for the propagation of replication-incompetent viral vectors is considered to be the best choice for gene therapy purposes.

Early adenovirus vectors (sometimes referred to as first generation adenovirus vectors, or singly deficient vectors) relied on deletions (and insertions) in coding regions E1 and/or E3 of the viral genome (see, for example, U.S. Pat. No. 5,670,488; U.S. Pat. No. 5,698,202; U.S. Pat. No. 5,731,172). E3 deletion was usually performed to provide the necessary space for the insertion of foreign genes of a limited size. The E3 region is non-essential for virus growth in tissue culture, so that vectors deleted only in E3 region could be propagated in non-complementing cells. As E1 region is essential for the virus growth, E1-deleted vectors could only be propagated in complementing cells, such as human 293 cells (ATCC CRL 1573), a human embryonic kidney cell line containing the E1 region of human Ad5 DNA.

One of critical issues in the development of safe viral vectors is to prevent the generation of replication-competent virus during vector production in a packaging cell line or during the gene therapy treatment. This may happen as a result of a recombination event between the genome of the vector and that of the packaging cells, or of the vector and the wild-type virus present in the recipient cells of the patient or introduced as a contaminant in the process of producing the recombinant virus. On occasion, a recombination event could generate a replication-competent virus carrying the transgene, which virus might spread to the environment. Even though recombination events are rare for E1-deleted adenovirus vectors, their in vivo replication and the ensuing risks could not be completely prevented, and generation of replication-competent adenovirus was demonstrated during the preparation of viral stocks. Another danger is the loss of replication deficiency (and the return to a phenotypic state of multiplication) through complementation in trans in some cells which produce proteins capable of replacing proteins encoded by the deleted regions of the viral genome. This was demonstrated for E1-deleted adenoviruses.

Attempts to improve the safety and cloning capacity of adenovirus vectors resulted in development of a new generation of multiply deficient adenovirus vectors (also referred to as second generation or multiply deleted vectors). Additionally to deletions in E1 and/or E3 coding regions, these vectors are also deleted in other regions of the viral genome essential for virus replication, such as early regions E2 and/or E4 (see, for example, WO 95/34671; U.S. Pat. No. 5,700,470; WO 94/28152) or late regions L1–L5 (see, for example, WO 95/02697). Other known approaches to improve the safety of adenovirus vectors include, for example, relocation of protein IX gene in E1-deleted adenovirus (U.S. Pat. No. 5,707,618) and inactivation of the gene IVa2 in a multiply deleted adenovirus (WO 96/10088). All second generation adenovirus vectors are replication-deficient and require complementing cell lines for their propagation, to restore in trans the deleted or inactivated functions of the viral genome. More importantly, such vectors show an improved resistance to recombination when propagated in complementing cell lines or transferred into recipient cells of a patient, making recombination events virtually nonexistent and improving the safety of gene therapy treatments.

Even though adenovirus vectors with improved resistance to recombination are known in the prior art, as exemplified above, they are not equal in terms of their gene transfer efficiency, cloning capacity, toxicity to host cells, severity of immune response induced in patient's organism, ease of propagation (which may be limited by toxicity of viral gene(s) to packaging cell lines), ease of generation (which may be limited by an expression cassette harboring toxic genes), and in vivo regulatability of the exogenous (foreign) gene expression. Consequently, there exists a continuous need for adenoviral vectors having at least some of these properties improved. The present invention provides new adenoviral vectors and complementing cell lines for their generation and propagation, which are free of many prior art limitations.

Adenoviral vectors may also be useful as tools for the production of proteins, for example for the purpose of functional genomics studies in mammalian cells. Cloning and expressing numerous genes allows the generation of mini-libraries useful for various applications, such as signal transduction studies or screening antisense DNA constructs. This application of adenoviral vectors requires a cloning system in which generation and selection of recombinant mutants can be easily performed. The present invention provides such a novel system of cloning DNA sequences using adenoviral vectors.

SUMMARY OF THE INVENTION

The present invention provides an adenovirus vector/packaging cell line system in which the vector replication is blocked by deletion of a single gene, not a viral region, which deletion does not interfere with any other viral functions. The deleted gene is the gene of the adenovirus protease. The protease encoded by the deleted gene is expressed in a complementing (packaging) cell line through a regulatable expression cassette which induces no toxic effects in the cells, thus making the generation and production of the vector easier and efficient. As the deleted gene is highly specific of adenovirus, no complementation of the gene in transduced cells is to be expected, which increases the safety and suitability of the protease gene deleted vectors for gene transfer purposes.

When additionally deleted for E1 region of adenoviral genome, the vectors of the invention are blocked for replication, but are capable of a single round of replication if deleted only for the protease gene. The latter feature permits an enhanced expression of the transgene in transduced cells, which may be of importance in some applications, for example to achieve localized enhanced expressions of transgenes (in situ tumor therapy) or efficient vaccinations without boosting.

The invention further allows positive selection of E1-deleted, protease-deleted recombinant adenovirus vectors by providing the protease gene as part of an expression cassette inserted in place of the E1 region in a shuttle vector. In vivo recombination of the shuttle vector with a protease-deleted adenoviral genome generates viable recombinants only when rescuing the protease cloned in E1 region. Non recombinant viral genomes are not able to grow due to the protease deletion, ensuring that only recombinant viral plaques are generated.

Consequently, it is an object of the present invention to provide novel cell lines capable of hosting an adenovirus mutant deleted for the protease gene, which cell lines contain DNA expressing the adenovirus protease.

It is a further object of the present invention to provide a method for producing novel cell lines capable of hosting an adenovirus mutant deleted for the protease gene, which cell lines contain DNA expressing the adenovirus protease.

It is a further object of the present invention to provide a method of using cell lines capable of hosting an adenovirus mutant deleted for the protease gene and containing DNA expressing the adenovirus protease to generate and propagate adenovirus mutants deficient for the adenovirus protease gene.

It is a further object of the present invention to provide novel adenovirus mutants deleted for the adenovirus protease gene.

It is a further object of the present invention to provide novel adenovirus mutants deleted for the protease gene and at least one additional adenovirus gene or genomic region.

It is a further object of the present invention to provide novel adenovirus vectors for gene transfer, protein production, gene therapy and vaccination, said vectors deficient at least for the adenovirus protease gene and containing at least one exogenous gene to be transferred to and expressed in a host cell.

It is a further object of the present invention to provide a novel means of generating recombinant adenovirus vectors by positive selection of recombinants deleted for the endogenous protease, in which the protease gene is rescued by cloning the gene in another region of the adenoviral genome.

According to one aspect of the present invention, novel cell lines have been generated which are capable of expressing the Ad2 protease gene from a dicistronic expression cassette, under control of a tetracycline inducible promoter. The protease is expressed in these cells together with the green fluorescent protein (GFP), the latter used to facilitate cell cloning and expression monitoring. The novel cell lines have been prepared by transfecting derivatives of 293 cells with pieces of DNA encoding the Ad2 protease and GFP, selecting cells harboring these pieces (cells expressing the GFP) and amplifying them. The novel cell lines, stably expressing the Ad2 protease, produce amounts of protease equal to or greater than those reached after comparable infections by adenovirus. The biological activity of the novel cell lines has been demonstrated by their ability to fully support the reproduction of Ad2ts1 mutant, a temperature-sensitive mutant expressing a functionally defective protease and to restore normal yields of replication of two novel adenovirus mutants in which the protease gene has been deleted.

According to another aspect of the present invention, novel mutants of Ad5 deleted at least for the adenovirus protease gene have been generated. These novel mutants have been successfully propagated in the cell lines of the invention.

According to yet another aspect, the present invention provides a method of generating protease-deleted adenovirus mutants having an exogenous gene inserted in E1 coding region, using positive selection of mutants obtained by in vivo recombination of adenoviral genome deleted for endogenous protease gene and in E1 coding region with a fragment of adenoviral genome expressing the adenoviral protease gene from an expression cassette replacing the E1 coding region.

BRIEF DESCRIPTION OF THE DRAWINGS

FIG. 5 is a schematic representation of the molecular cloning performed to generate recombinant adenoviral vectors by positive selection with Ad protease. The recombinant represented here featured an E1-deletion. A shuttle vector, containing adenovirus 59.4 to 15.5 mu part of the genome to allow recombination, also harbored a triple expression cassette containing, among others, the protease gene and a foreign gene of interest (X) in place of the E1 region. After linearisation, the shuttle vector was cotransfected in a 293-derived cell line with a protease-deleted adenovirus genome cleaved in E1. Due to protease deletion, only genomes for which recombination, and thus the rescue of the protease gene, has occurred, produced viral plaques. The resulting recombinant viruses harbored no protease gene in L3 region, but the E1-cloned gene and the protease are ectopically expressed from the E1 region.

DETAILED DESCRIPTION OF THE PREFERRED EMBODIMENTS

As used herein, the term "adenovirus" (Ad) means any adenovirus of human, mammalian, or avian origin (Mastadenovirus, Aviadenovirus families). Of those, human adenoviruses Ad2 and Ad5 are preferred, Ad5 being particularly preferred.

In the context of the present invention, the term "adenovirus protease" designates the protease of any adenovirus of human, mammalian, or avian origin, including analogues, homologues, mutants and isomers of such protease. The term "adenovirus protease gene" means the protease gene of any adenovirus of human, mammalian, or avian origin, including analogues, homologues, mutants and isomers of such gene. Even though minor differences exist between proteases of different adenoviruses, these proteases are interchangeable. Proteases of human adenoviruses Ad2 and Ad5 are preferred, the Ad2 protease being particularly preferred.

The adenovirus protease, first identified by studies on the Ad2ts1 temperature sensitive mutant (Weber, *J. Virol*, 17, 462–471 (1976); Yeh-Kai et al., *J. Mol. Biol.*, 167, 217–222 (1983)), is a key enzyme in the adenovirus life cycle, serving for maturation of several proteins. Proteins cleaved by this enzyme are the pre-terminal protein (pTP), pVI, pVII, pVIII, pIIIa and the 11 K DNA binding proteins (Anderson et al., *J. Virol.*, 12, 241–252, (1973); Boudin et al., *Virology*, 101, 144–156 (1980); Tremblay et al., *Biochim. et Biophys. Act.*, 743, 239–245 (1983)). In addition to those substrates, the cleavage of viral 52K protein (Hasson et al., *J. Virol.*, 66, 6133–6142 (1992)) and of cellular cytokeratin 18 (Chen et al., *J. Virol.*, 67, 3507–3514 (1993)) play an important role in the viral cycle. The adenovirus protease is therefore an essential element for virus proteins maturation, for virus entry into host cells (Cotten et al., *Virology*, 213, 494–502, (1995); Greber et al., *EMBO J.*, 15, 1766–1777 (1996)) and for release of virions from infected cells (Chen et al., supra).

Adenovirus protease deleted mutants provide numerous advantages for gene therapy and vaccination. Such mutants, whether deleted or not for additional genes (e.g., in the E1 coding region), are completely replication-deficient. Even though capable of cleaving some cellular proteins, the adenovirus protease is highly specific, making it extremely unlikely that the protease defect in the mutant could be overcome in a mammalian cell, an effect demonstrated for E1 deleted adenovirus mutants in some mammalian cells (Hela and teratocarcinoma stem F9 cells: Imperiale et al., *Mol. Cell. Biol.*, 4, 867–874 (1984), Nevins et al., *Curr. Top. Microbiol. Immunol.*, 113, 15–19 (1984); embryonic carcinoma (EC): Keaveney et al., *Nature*, 365, 562–566 (1993)). This provides an increased safety level for therapeutic applications. For gene therapy applications, a complete blockage of replication of adenovirus can be reached by deleting the protease gene together with other gene or genes essential to the virus growth, such as E1 coding region. Recombinant vectors deleted only for the protease and thus capable of a single round of replication provide interesting vectors for vaccination.

Adenoviruses deleted for the protease gene require for their propagation a cell line capable of providing the protease gene product in trans, such as the cell lines of the present invention. According to one preferred embodiment, 293S cell lines stably expressing the Ad2 protease (293-PS cells) have been generated. 293S cells were chosen for two reasons. Firstly, 293 cells allow the propagation of adenoviruses simultaneously deleted in E1 and/or E3 coding region, such as recombinant adenovirus vectors for gene therapy applications. Secondly, the non-adherent phenotype of 293S cells is advantageous for a scale-up of preparation of deleted adenovirus (Garnier et al., *Cytotechnology*, 15, 145–155 (1994)), for example for the production of vector stocks. It would be apparent to those skilled in the art that other cell lines capable of hosting adenoviruses, such as A549, 911, or BMAdE1 would be also suitable for generating cell lines expressing the adenovirus protease gene.

According to the preferred embodiment of the invention, inducible promoters were chosen to achieve regulatable expression of the protease gene in the cell lines of the invention, namely the tTA and rtTA systems (Gossen et al., *Proc. Natl. Acad. Sci. USA*, 89, 5547–5551 (1992); Gossen et al., *Science*, 268, 1766–1769 (1995)). These systems allow for inducible expression of the gene, either by adding or withdrawing tetracycline to the cells. Regulatable expression cassettes were chosen because of the ability of the adenovirus protease to disrupt some components of the cellular cytokeratin network (Chen et al., supra). This function appears to play a key role in the phenotypic characteristics of adenovirus cytopathic effect, and thus may be at least deleterious for the host cells. A regulatable expression cassette makes it possible to limit the expression of the protease, at least at a high level, only to periods of time when the inducer is either added or withdrawn, so that the toxic effect of protease which could hamper the generation or propagation of protease-deleted adenovirus is eliminated. (Cells transfected by foreign plasmid DNA are stressed by transfection and much more sensitive to any toxic effects.)

For recombinant adenovirus vectors for gene therapy and vaccination, putting the transgene into a similar regulatable expression cassette provides a number of advantages. By choosing, for example, either tTA or rtTA regulation system, this allows the control of expression of the transgene either by administering tetracycline or by withdrawing its administration, respectively. This can be useful, for example, in vaccination of animals for which tetracycline is added on a regular basis to feeding. Expression of the gene of interest can be in this case induced by withdrawing the administration of tetracycline during an appropriate period of time. It would be apparent to those skilled in the art that other regulatable promoters, such as ecdysone or corticosteroid responsive systems could be used for the practice of the invention.

The cell lines of the invention can be prepared by methods known to those skilled in the art, in particular by cotransfection of cells capable of hosting adenovirus with pieces of DNA encoding the adenovirus protease and pieces of DNA encoding a selection factor, incubating the cells, selecting cells expressing the selection factor, and amplifying those expressing the adenovirus protease. The selection factor can be anything which will allow the selection of a cell, such as, for example, an antibiotic resistance protein.

According to the preferred embodiment, the novel complementing cell lines of the invention were produced by cotransfecting 293-tTA or 293-rtTA cells with plasmid pTR5/PS-DC/GFP (which contains a tetracycline regulatable (TR) promoter in a dicistronic cassette (DC) with the GFP and the protease (PS) gene) and with plasmid pTKNeo (comprising the gene of resistance to geneticin (antibiotic G418)) or with plasmid p3'SS (comprising the gene of resistance to hygromycin), respectively, and selecting transfected cells with these antibiotics. Antibiotic-resistant colonies expressing the GFP protein were amplified and several of them selected for further analysis.

To facilitate the screening of recombinant clones, the adenovirus protease gene was expressed from a dicistronic cassette (Mosser et al., *Biotechniques*, 22, 150–161 (1997)) together with a reporter gene of *Aquorea victoria* green fluorescent protein (GFP) (Prasher et al., *Gene*, 111, 229–233 (1992); Heim et al., *Nature*, 373, 663–664 (1995)).

After the first selection with an antibiotic (G418 or hygromycin), cells expressing GFP were selected for further studies by automated fluorescent cell sorting. This system allowed an efficient generation of 293 cell lines stably expressing the active Ad2 protease.

It will be apparent to those skilled in the art that the pieces of DNA encoding the adenovirus protease may be introduced into the cells using any DNA intracellular delivery system, such as, for example, recombinant plasmids, and by means of any transfection technique, such as calcium phosphate precipitation or liposome technology. Also, cells harboring pieces of DNA encoding the adenovirus protease may be made selectable using any suitable selection factor, such as the gene of resistance to an antibiotic, which gene can be transfected into the cells by a suitable recombinant plasmid.

To study the biological activity of the recombinant protein, complementation of the Ad2ts1 mutant (Weber, J. Virol., 17, 462–471 (1976)) was examined. This mutant encodes a modified P137L protease which is active at the permissive temperature (33° C.) and functionally defective at 39° C. Replication of the Ad2ts1 on 293-tTA-PS and 293-rtTA-PS cell lines allowed for restoration of yields similar to that of the wild-type virus. It was also shown that expression of the protease was not toxic to the cells but rather slightly impaired the normal cell growth. The novel cell lines were also shown to restore replication of two novel adenovirus mutants in which the protease gene has been deleted.

The novel adenovirus mutants deleted for the protease gene can be prepared by methods known to those skilled in the art. In general, the preparation of a virus mutant relies on preparing first the complete genome of the mutant by joining suitable pieces of DNA, either by ligation in vitro or by recombination in a cell. In the latter case, several (usually two or three) fragments of adenoviral DNA containing regions of similarity (or overlap) are transfected into host cells, where they become recombined into a full-length viral genome. The fragments to be ligated or recombined may contain deletions and modifications with respect to the wild type viral genome, but must otherwise contain its entire length. The DNA of the recombinant virus so prepared is then transfected into suitable complementing cells capable of providing in trans viral functions missing from the transfected recombinant viral genome as a result of the deletions and modifications introduced into the wild type genome. The recombinant virus will multiply in these cells from which it can be subsequently released, for example by subjecting cells to several freeze-thaw cycles. Numerous variations of this general procedure are possible, as would be apparent to those skilled in the art.

According to the preferred embodiment, two novel Ad5 mutants (designated as Ad5CMVLacZ-CMVGFP-ΔPS and Ad5-ΔPS, respectively) have been generated according to the general procedure outlined above. This was achieved by a series of clonings into bacterial plasmids, followed by recombination of suitable fragments of the viral genome performed in E. coli, to generate bacterial plasmids harboring protease deleted adenovirus genomes. This procedure is summarized in FIG. 2 and FIG. 3 and discussed in more detail in the following Examples.

Ad5-ΔPS mutant is deleted for the protease gene only. Ad5CMVLacZ-CMVGFP-ΔPS is deleted for the protease gene, but also in E1 and E3 coding regions of the Ad5 genome. Both mutants have been successfully propagated in the novel complementing cell lines of the invention expressing the Ad2 protease. Ad5CMVLacZ-CMVGFP-ΔPS mutant contains in its genome two exogenous genes (transgenes): the gene of E. coli β galactosidase (βgal) and the gene of Aquorea victoria green fluorescent protein (GFP). These reporter genes can be easily replaced with genes of therapeutic interest by methods known to those skilled in the art. In both mutants genes of therapeutic interest can be easily introduced by recombination, as both were cloned in bacterial plasmids.

The invention also allows an easy generation of E1-deleted, protease deleted recombinant vectors, comprising an exogenous gene or genes (transgenes) in E1 coding region, by providing the protease gene (together with exogenous gene or genes) as part of a di- or tricistronic cassette in place of E1 coding region in a shuttle vector. In vivo recombination of the shuttle vector with a protease-deleted adenoviral genome generates viable recombinants only when rescuing the protease gene cloned in E1 coding region. Non-recombinant adenoviral genoms are unable to grow due to protease deletion. This positive selection ensures that only recombinant vectors will be generated.

The invention also allows the safe generation of adeno-associated virus vectors due to the total block of replication of the protease deleted mutants that can be used as helpers for this application.

Experimental

The cell lines and vectors of the present invention have been prepared using techniques well known to those skilled in the art. The following examples are provided for better illustration of the invention.

Materials and Methods

Cells and Viruses 293 cells are human embryonic kidney cells expressing high levels of the adenovirus 5 E1A and E1B products (Graham et al., J. Gen. Virol., 36, 59–72 (1977)). 293S cells, a non-adherent 293 cells clone has been previously described (Garnier et al., Cytotechnology, 15, 145–155 (1994); Massie et al., Bio/Technology, 13, 602–608 (1995)). 293-tTA cell line was described by Massie et al., J. Virol, 72, 2289–2296 (1998), and the 293-rtTA cell line was obtained in a similar way. Adenovirus Ad2ts1 mutant was previously described (Weber, J. Virol., 17, 462–471 (1976)). Adenovirus d1309 is a fully replicative mutant and was previously described (Jones et. al., Cell, 13, 181–188 (1978)). AdCMV5-GFP is a recombinant adenovirus in which E1 region has been replaced by a CMV driven GFP expression cassette (Massie et al., Cytotechnology, in press (1999)).

Plasmids

Plasmid pTKNeo was generated by auto-ligation of the BstEII fragment of pREP 9 (Invitrogen). Plasmid pTR-DC/GFP was previously described (Mosser et al, 1997). This plasmid has been modified from pUHD10.3 (Resnitsky et al., Mol. Cell. Biol., 14, 1669–1679 (1994)) which contains the tTA-responsive promoter with a dicistronic expression cassette. Dicistronic expression is permitted by the encephalomyocarditis virus IRES (Ghattas et al., Mol. Cell. Biol., 11, 5848–5859 (1991)). The original pTR-DC/GFP was modified by insertion of a BglII site. Protease gene was excised from pAdBM5-PS, by BamHI digestion, sequenced and subcloned into the BglII site of pTR-DC/GFP. Final plasmid, pTR5/PS-DC/GFP thus co-expresses inducibly GFP S65T mutant and Ad2 protease genes. Expression of GFP and protease were assayed by transfection in 293 cells. The transient expression of the protease was established by Western-blot with an anti-protease polyclonal antiserum raised in rabbit with a recombinant protein (from Dr J.

Weber, University of Sherbrooke). The expressed protein had the same molecular weight as the native protein from wild-type adenovirus, and was expressed only when induced. Plasmid pDE3 was a gift of Dr Lochmüller (Montreal Neurological Institute). This plasmid contains the right end of Ad5 genome from the BamHI site (21562) to the end of the genome, with an E3 deletion. This deletion corresponds to the one described by Bett et al. (1994) and originates from plasmid pBHG11 (extent of the deletion: 27865–30995). Plasmid pAdEasy-1-βGal-GFP was a gift of Dr He (John Hopkins University, Baltimore, Md.) and has been already described (He et al, 1998). Plasmid pTG3602 (Chartier et al., 1996) was a gift of Dr Mehtali (Transgene SA, Strasbourg, France). Recombinant adenovirus construction in *E. coli* was performed as described respectively by He et al (1998) and Chartier et al. (1996).

Generation of Protease Expressing Cell Lines 293-tTA cell lines were generated by co-transfection of pTR5/PS-DC/GFP and pTKNeo. 293 rtTA-PS clones were generated in a similar way by co-transfecting the same plasmid with the p3'SS (Stratagene) in 293S rtTA. Transfections were achieved by the optimized calcium-phosphate precipitation method (Jordan et al, *Nucleic Acids Res.*, 15, 24(4): 596–601(1996)). For tTA and rtTA, selection drugs were respectively G418 and hygromycin (Sigma Chemical).

Selection of Recombinant Cell Clones

After co-transfection and selection, clones of 293S cells expressing the GFP from the dicistronic cassette were selected by screening for the expression of the GFP by flow cytometry analysis and cell sorting. Flow cytometry was performed using an EPICS Profile II (Coulter, Hialeah, Fla., USA) with a 15 mW argon-ion laser. Cell sorting was carried out on an EPICS V (Model 752, Coulter) multiparameter laser flow cytometer and cell sorter, using the Auto-clone (multiwell automated cell deposition) system. Before selection and sorting, expression of both GFP and protease was induced by addition (rtTA) or suppression (tTA) of doxycycline. For the analysis of GFP expression, cells were sterily collected and concentrated ($1\times10^6$ cells/ml) in phosphate-buffered saline (PBS) by centrifugation. The mostly fluorescent cells were gated and distributed clonally in 96-well plates.

Analysis of Recombinant Protein Expression

Expression of the GFP was checked periodically by flow cytometry analysis, while expression of the protease was assayed by western-blotting. Cells were washed in PBS, centrifuged and frozen. Lysis was carried out in 100 mM Tris-HCl [pH 6.9], 10% glycerol, 2% SDS, and high molecular weight DNA was disrupted by sonication. Prior to assay, total protein contents of extracts were titrated using the DC Protein Assay Kit (Biorad). For electrophoresis, samples were diluted in Laemmli buffer (Laemmli et al., *J.Mol.Biol.*,88, 749–165, (1974)) and boiled for 5 min. An estimated 20 μg total protein quantity was loaded per well in 14% acrylamide:bisacrylamide (30:1) gels. After electrophoresis, proteins were transferred to nitrocellulose membranes which were subsequently blocked overnight at 4° C. with PBS containing 5% nonfat dry milk, 0.1 % Tween 20. The rabbit anti-protease antibody was diluted 1:20000 in the same buffer but with 0.2% Tween 20. As an internal control, an anti-actin monoclonal antibody diluted 1:10000 was used. Incubation was overnight at 4° C. Conjugates were used at a 1:10000 dilution in the same buffer for 1 hr at room temperature. Revelation was carried out using the ECL chemiluminescence kit (Amersham) according to the manufacturer's instructions.

EXAMPLES

Generation and Isolation of 293 Cell Lines Transformed with Ad2 Protease Gene

Cell lines were generated by co-transfection and selection with appropriate agents as summarized in Table 1.

TABLE 1

Analysis of the clones obtained from transformation of 293 cells with protease

| Cells | Plasmids used for transfection | Selection agent | Clones obtained | Clones analyzed | Selected Positive clones |
|---|---|---|---|---|---|
| 293 tTA | pTR5/PS-DC/GFP + pTKNeo | G418 | >50 | 17 | 7 |
| 293 rtTA | pTR5/PS-DC/GFP + p3'SS | hygromycin | >50 | 14 | 9 |

293 tTA cells were co-transfected with pTR5/PS-DC/GFP and pTKNeo, while 293 rtTA were co-transfected with the same plasmid and p3'SS. After a 48 hour recovery, transfected cells were submitted to a three weeks selection by either G418 (500 μg/ml) for 293 tTA or hygromycin (150 μg/ml) for 293 rtTA. During this time, fresh medium and drug were applied to cells twice a week. Throughout the selection process, GFP expression was monitored on aliquots by flow cytometry analysis. Cells were then sorted using the multiwell automated cell deposition system and clonal distribution was visually checked. Expression was then assessed and only homogenous clones (as checked by unicity of the peak of fluorescent cells) were selected. Results of GFP expression of stable clones are summarized in Table 2.

TABLE 2

GFP expression and induction efficiency in 293-tTA-PS and 293-rtTA-PS

| Clone | FI OFF | FI ON | Induction Factor |
|---|---|---|---|
| 293-tTA-PS-2 | 138 | 2838 | 20 |
| 293-tTA-PS-11 | 63 | 1322 | 21 |
| 293-tTA-PS-15 | 30 | 3186 | 106 |
| 293-rtTA-PS-7 | 35 | 1228 | 35 |
| 293-rtTA-PS-10 | 107 | 720 | 7 |
| 293-rtTA-PS-17 | 118 | 1654 | 14 |

Selected cell line clones were tested for the expression of the GFP (basal and induced) by flow cytometry analysis. FI: fluorescence index calculated as the percentage of cells expressing GFP by the mean fluorescence value; OFF: GFP expression without induction (50 ng doxycline per ml for tTA); ON: GFP expression after induction (1 μg per ml for rtTA). Induction factor was calculated as the ratio between the FI of the ON state and the FI of the OFF state.

Of all the tested clones, three of 293S-tTA-PS and three of 293S-rtTA-PS clones were selected. Induction efficiency was measured by comparing products of the mean fluorescence of one cell by the percentage of fluorescent cells (fluorescence indexes: FI). Induction factors ranged from 7 to 106 which is in the range of what is usually observed with tetracycline-regulated expression cassettes.

Protease Expression in 293-tTA-PS and 293-rtTA-PS

Figure 1:
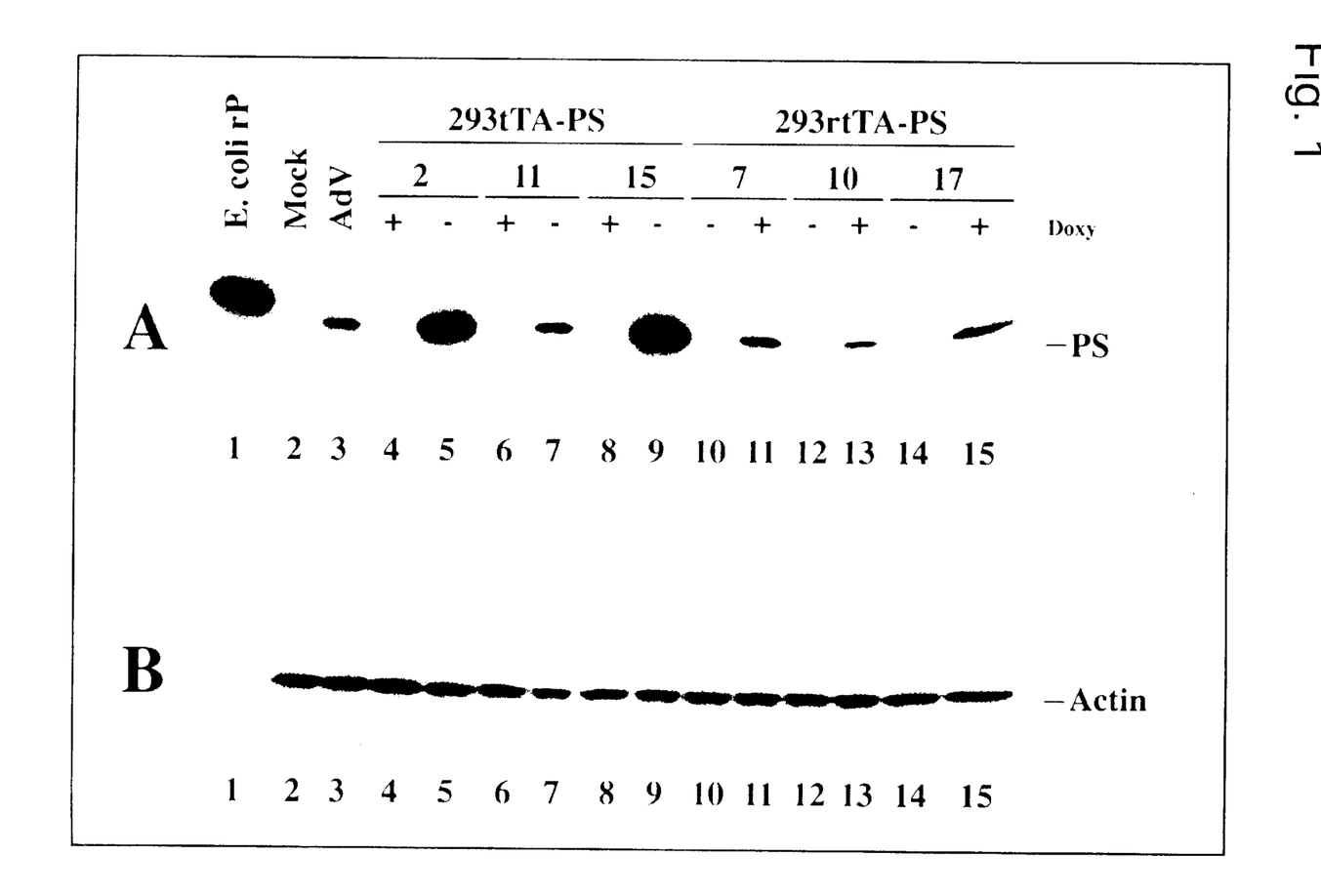
FIG. 1A is a photograph showing expression of the protease by some clones of 293-tTA-PS and 293-rtTA-PS cells. Total protein extracts (30 μg) from different cell lines before (−) and after (+) induction were submitted to 14% SDS PAGE and transferred to nitrocellulose sheet. E. coli expressed Ad2 protease (lane 1: E. coli), adenovirus endogenous protease (lane 3: AdV) and non-transformed cells (lane 2: mock) were included as controls.
FIG. 1B is a photograph showing immunoblot of protein extracts of FIG. 1A. Proteins were revealed with an antiactin antibody to check that the same amount of protein was loaded per well.

Of the clones tested for protease expression, three clones of 293-tTA-PS and of 293-rtTA-PS are presented (FIG. 1A). Expression was revealed with a polyclonal rabbit anti-serum raised to the *E. coli*-expressed protein. Results demonstrate that the expressed protein displays the same electrophoretic pattern than that of the endogenous adenovirus protein, and that the expression depends on the induction in all tested clones. The latter assertion was checked by the internal control (cellular actin) which demonstrates that the same amount of protein extract has been loaded in each well. Testing of all obtained clones of rtTA did not allow for observation of higher levels of expression than that reached with tTA clones. Level of expression of protease in all selected clones were equal or higher than that of the native adenovirus protease (FIG. 1A, lane 3). To check that, 293 cells were infected at a MOI of 10 pfu with AdCMV5-GFP (Massie et al, *Cytotechnology*, in press (1999)) and protein extracts were prepared at 48 hrs p.i. Similar level of expression was achieved with the clones derived from 293-tTA and 293-rtTA cells.

Biological Activity of Protease Expressed by Cell Lines

To study the biological activity of Ad2 protease in transformed cell lines, complementation of the temperature-sensitive Ad2ts1 and of two novel protease deleted mutants by the cell lines was examined. Ad2ts1 viral particles produced at 39° C. contain a functionally deficient protease, and they were used to assess complementation. Results of one-step growth curves in 293 and 293-PS cell lines (tTA and rtTA) for Ad2ts1 are summarized in Table 3 and for both novel protease deleted mutants in Table 4.

TABLE 3

Yield of dl309 and Ad2ts1 from One-Step growth curves in different 293-derived cell lines

| Virus | Cell line | Temperature | Virus titer |
|---|---|---|---|
| dl309 | 293-tTA | 33 | $1.7 \times 10^8$ |
|  |  | 39 | $1.2 \times 10^8$ |
|  | 293-tTA-PS-15 NI | 33 | $2.0 \times 10^8$ |
|  |  | 39 | $1.2 \times 10^8$ |
|  | 293-tTA-PS-15 I | 33 | $8.1 \times 10^7$ |
|  |  | 39 | $7.0 \times 10^7$ |
|  | 293-rtTA | 33 | $1.6 \times 10^8$ |
|  |  | 39 | $1.5 \times 10^8$ |
|  | 293-rtTA-PS-7 NI | 33 | $1.5 \times 10^8$ |
|  |  | 39 | $1.0 \times 10^8$ |
|  | 293-rtTA-PS-7 I | 33 | $7.8 \times 10^7$ |
|  |  | 39 | $7.2 \times 10^7$ |
| Ad2ts1 | 293-tTA | 33 | $2.5 \times 10^8$ |
|  |  | 39 | $5.0 \times 10^3$ |
|  | 293-tTA-PS-15 NI | 33 | $1.6 \times 10^8$ |
|  |  | 39 | $9.0 \times 10^7$ |
|  | 293-tTA-PS-15 I | 33 | $4.0 \times 10^7$ |
|  |  | 39 | $5.0 \times 10^7$ |
|  | 293-rtTA | 33 | $2.0 \times 10^8$ |
|  |  | 39 | $2.0 \times 10^3$ |
|  | 293-rtTA-PS-7 NI | 33 | $1.5 \times 10^8$ |
|  |  | 39 | $3.2 \times 10^8$ |
|  | 293-rtTA-PS-7 I | 33 | $8.0 \times 10^7$ |
|  |  | 39 | $5.8 \times 10^7$ |

Cells were infected at a multiplicity of 2 plaque-forming unit (p.f.u) per cell. 2–3 days later at 39° C. or 5 days later at 32° C., cells were harvested, frozen-thawed three times, and subsequent extracts were titrated. Results of a typical experiment are presented here. Titers were determined as p.f.u. on 293 cells at 33° C. NI: non-induced, I: induced expressions. Experiments carried out at 33° C. were included as controls.

While Ad2ts1 yielded respectively $5 \times 10^3$ p.f.u. and $2 \times 10^3$ p.f.u. at 39° C. in 293-tTA and 293-rtTA cell lines, complementation was evidenced by the obtention of titers similar to that of the dl309 mutant in protease expressing cell lines. Induction had the effect of slightly decreasing titers, but surprisingly, basal expression of the gene from 293-tTA-PS-15 and 293-rtTA-PS-7 was sufficient to complement the Ad2ts1 mutant. There was no difference between tTA and rtTA complementing cell lines.

To further demonstrate the biological activity of cell lines and to characterize novel Ad5 mutants, one-step growth curves in 293-tTA/rtTA and 293-tTA/rtTA-PS cell lines were generated (Table 4).

TABLE 4

Yield of Ad5CMVLacZ-CMVGFP-ΔPS and of Ad5-ΔPS with corresponding controls from One-Step growth curves in different 293-derived cell lines.

| Virus | Cell line | Virus Titer |
|---|---|---|
| Ad5CMVLacZ-CMVGFP-ΔPS | 293-tTA/rtTA | $<10^4$ |
|  | 293-rtTA-PS-7 NI | $10^8$ |
|  | 293-rtTA-PS-7 I | $6.0 \; 10^7$ |
|  | 293-tTA-PS-15 NI | $1.4 \; 10^8$ |
|  | 293-tTA-PS-15 I | $5.0 \; 10^7$ |
| Ad5CMVLacZ-CMVGFP | 293-tTA/rtTA | $6.3 \; 10^8$ |
|  | 293-rtTA-PS-7 NI | $6.5 \; 10^8$ |
|  | 293-rtTA-PS-7 I | $1.2 \; 10^8$ |
|  | 293-tTA-PS-15 NI | $5.0 \; 10^8$ |
|  | 293-tTA-PS-15 I | $10^8$ |
| Ad5-ΔPS | 293-tTA/rtTA | $<10^4$ |
|  | 293-rtTA-PS-7 NI | $1.4 \; 10^8$ |
|  | 293-rtTA-PS-7 I | $7.0 \; 10^7$ |
|  | 293-tTA-PS-15 NI | $1.5 \; 10^8$ |
|  | 293-tTA-PS-15 I | $5.2 \; 10^7$ |
| Ad5 | 293-tTA/rtTA | $6.0 \; 10^8$ |
|  | 293-rtTA-PS-7 NI | $6.5 \; 10^8$ |
|  | 293-rtTA-PS-7 I | $1.0 \; 10^8$ |
|  | 293-tTA-PS-15 NI | $6.5 \; 10^8$ |
|  | 293-tTA-PS-15 I | $1.0 \; 10^8$ |

Cells were infected at a multiplicity of 2 plaque-forming unit (p.f.u) per cell. 2–3 days later, cells were harvested, washed three times in PBS, frozen-thawed three times, and subsequent extracts were titrated. Results of a typical experiment are presented here. Titers were determined as p.f.u. on 293 cells. NI: non-induced, I: induced expression.

Biological activity was also demonstrated by the ability of the 293-rtTA-PS-7 clone to generate protease deleted mutants Ad5CMVLacZ-CMVGFP-ΔPS and Ad5-ΔPS after transfection of recombinant DNA. As expected, while the protease deleted mutants were unable to grow in 293-rtTA, complementation by cell lines allowed for the restoration of viral titers close to those of the controls (which are exactly the same viruses as the mutants, except for the presence of the protease gene). It is noteworthy that as for Ad2ts1, basal protease expression from both tTA and rtTA complementing cell lines is sufficient to complement the protease deleted mutants. It is also noteworthy that in the induced state of expression of the protease, viral yields were slightly decreased.

Growth Rate of 293-PS Cell Lines

Figure 4:
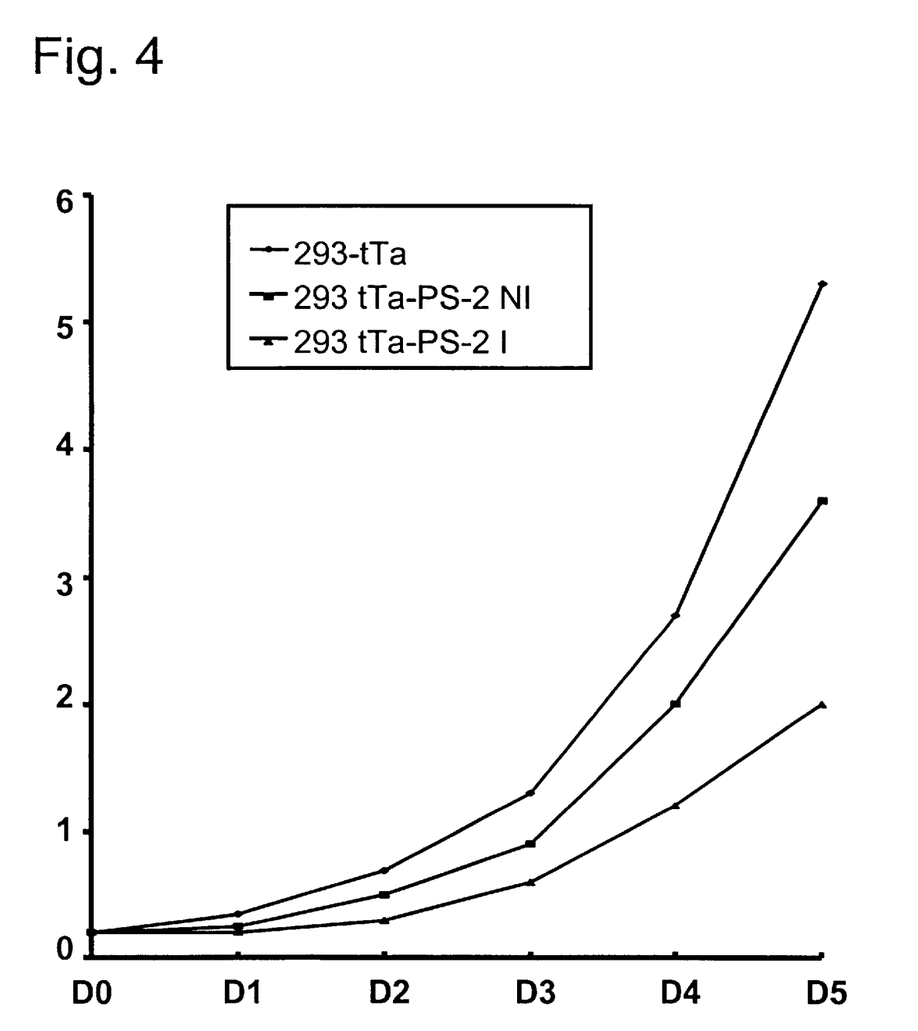
FIG. 4 is a graph showing the effects of induction of protease expression on viability of cells of 293-PS cell lines. Six 6 cm Petri dishes were seeded with $2 \times 10^5$ cells of 293 and 293-PS tTA. Aliquots were examined for living/dead cells by trypan blue staining on day 0 (D0) through day 5 (D5). Results of overall cell growth of a typical experiment are plotted as the count of total living cells as a function of time (in days) for 293-tTA-PS cells, either induced (I) or not induced (NI), with 293-tTA as controls.
Figure 5:
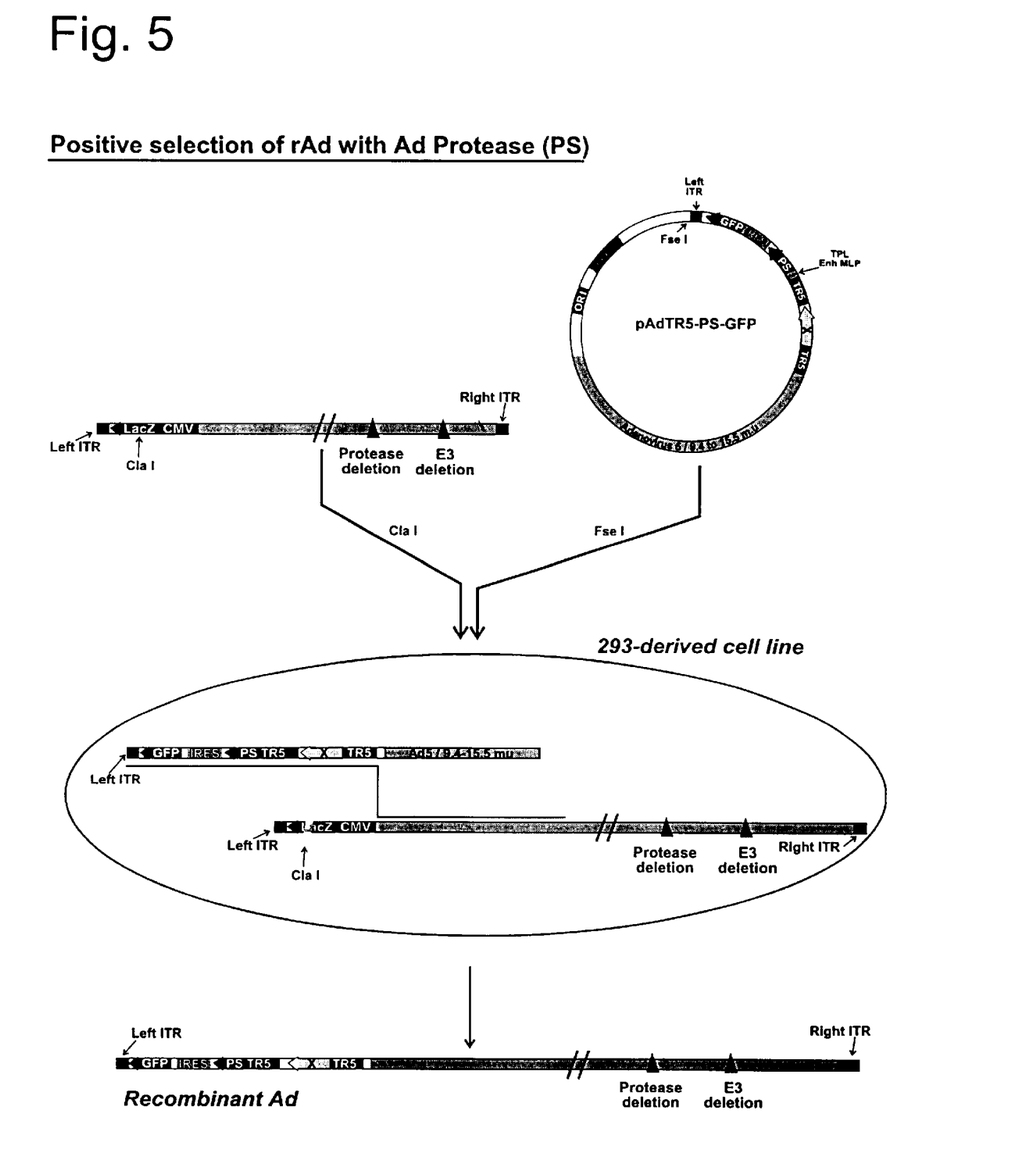

Visual examination of 293-PS cell lines showed that after induction of expression cells did not displayed a significantly different phenotype. To further study the effect of induction on cell lines, viability of cells was measured by counting living cells, either induced or not, after trypan blue staining every day from D0 to D5. For 293-rtTA-PS cells, there was no difference between induced or non-induced cells. For one clone of 293-tTA-PS (clone 2), results are represented in FIG. 4. It can be seen that the expression of the protease had no significant deleterious effect on cells growth. It is clear as well that as no effect could be evidenced during a period (24–48 hrs) compatible with the production of a recombinant adenovirus mutant, these cell lines will be useful for generation and expansion of protease-deprived mutants. Expression of the gene did not show a toxic effect, but rather a slight cell growth impairment: when maintained in the induced state of protease expression, cells growed slower. Given that overexpression of the protease could slightly impair cell growth as well as reducing viral yields, controlling its expression with a regulatable promoter was paramount both for obtaining the best protease complementing cell lines as well as for insuring maximal production of protease deleted AdV.

Stability of 293-PS Cell Lines

To check the stability of selected clones, cell lines maintained during 2 months without selection drug were assayed for the expression of the GFP and of the protease. Both proteins were expressed at levels similar to that of early passage cells as determined by respectively flow cytometry and immunoblot analyses (data not shown). No change in drug susceptibility was noticed after 2 months passages and neither did protease expression levels were modified.

Transfectability of 293 PS Cell Lines

Clones 293-tTA-PS-15 and 293-rtTA-PS-7 were analyzed for the ability to support the production of viral plaques after transfection with AdCMV-LacZ DNA. Both clones yielded as many viral plaques as respectively parental 293-tTA and 293-rtTA cells. 293PS cell lines were thus very efficiently transfected and were subsequently used for the generation of protease-deleted mutants.

Effect of Adenovirus Infection on Protein Expression

To study the effect of the expression of IVa2 products (Lutz et al., *J. Virol.*, 70, 1396–1405, (1996)) on the MLP enhancer that is included in our construction, cell lines were infected in triplicate at a MOI of 1 p.f.u. and GFP expression was followed in induced and non-induced cells. No significant difference could be evidenced between both batches.

Generation of Protease-deleted Mutants

Figure 2:
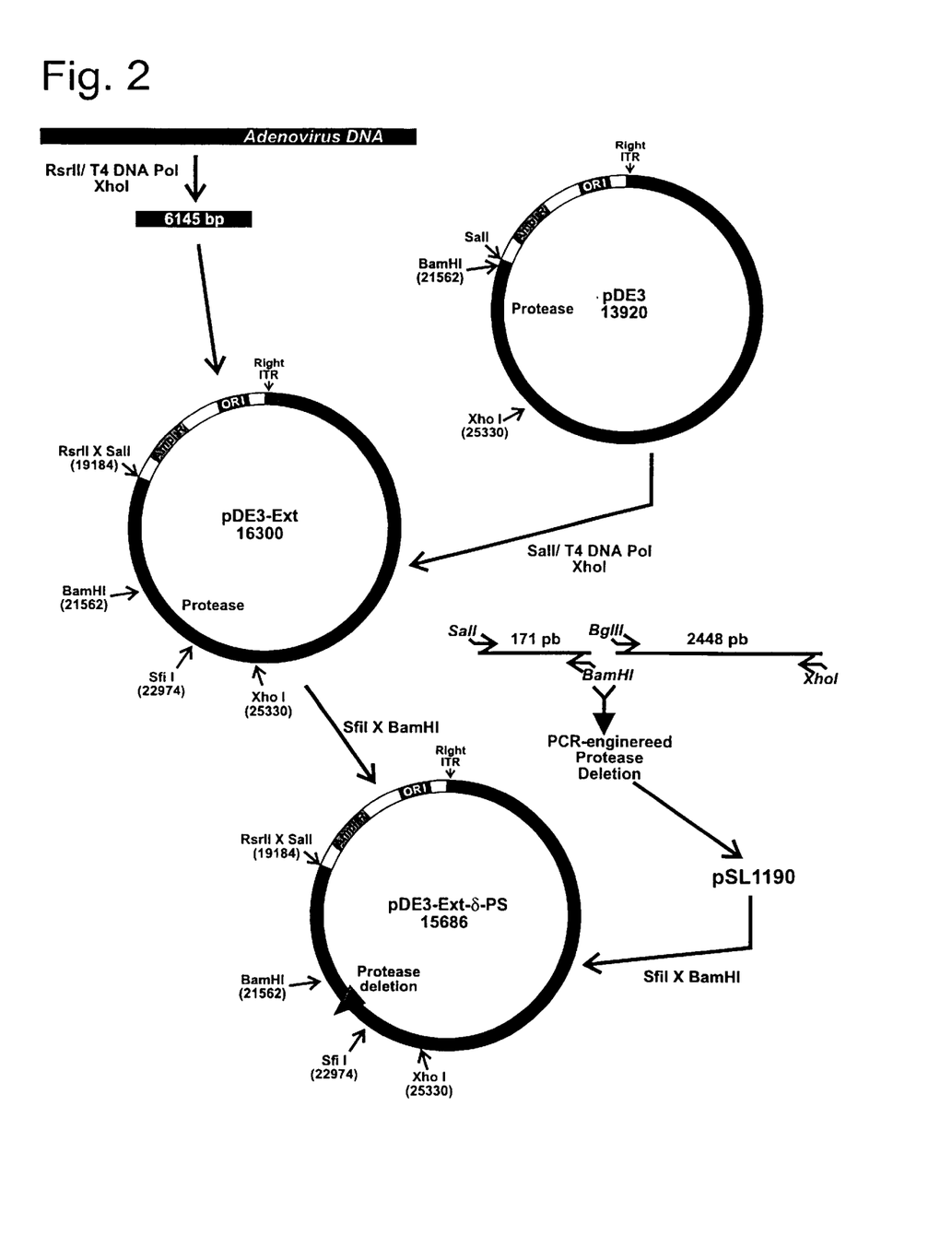
FIG. 2 is a schematic representation of all molecular clonings performed to generate bacterial plasmids harboring protease deleted adenovirus regions. A PCR engineered protease deletion was introduced (after sequencing of the corresponding region) into pDE3 plasmid in which a 2378 bp upstream extension has been previously inserted by cloning of the RsrII/XhoI 6145 bp fragment from Ad5 genome.
Figure 3:
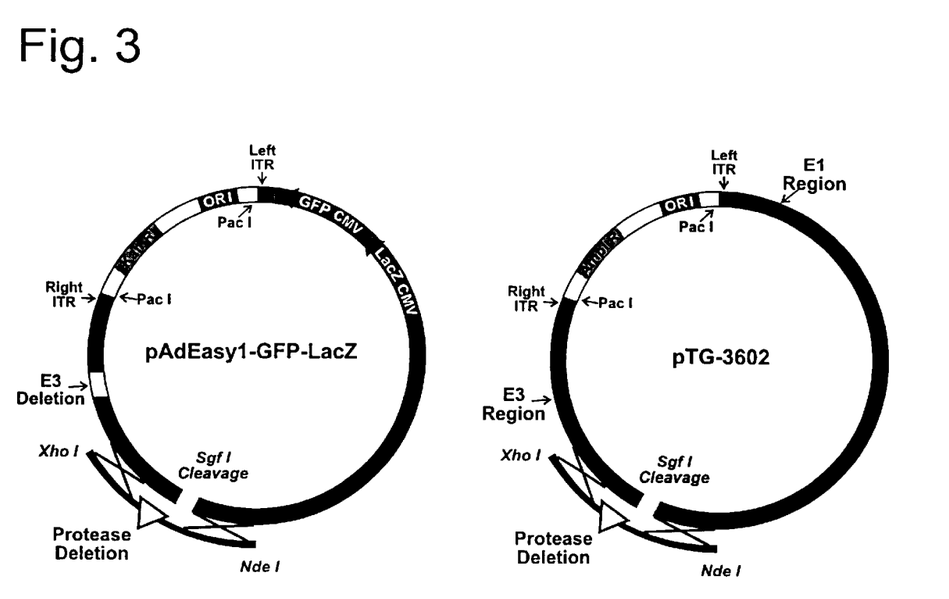
FIG. 3 is a schematic representation of bacterial plasmids harboring protease deleted adenovirus regions and of the recombinations performed in E. coli to generate bacterial plasmids harboring protease deleted adenovirus genomes. The NdeI/XhoI fragment from pDE3-ext-ΔPS plasmid was introduced by homologous recombination in E. coli with either pAdEasy1-βgal-GFP plasmid (which harbors an E1/E3 deleted Ad5 genome with reporter genes βgal of E. coli and GFP) or pTG3026 plasmid (which harbors an intact Ad5 genome) SgfI digested.

Plasmids clonings are summarized in FIG. 2. For the construction of protease-deleted mutants of Ad5, an extension sufficient for homologous recombination was first introduced in pDE3 plasmid by ligation of the 6145 bp fragment resulting from the RsrII/XhoI digestion of the Ad5 genome into the unique sites SalI and XhoI. To clone this insert and generate pDE3-ext plasmid, RsrII (from the insert) and SalI (from pDE3) were first T4 DNA polymerase repaired. Protease deletion was engineered by PCR to synthesize a 171 bp upstream fragment (forward primer: gtcgacCATGGACGAGCCCACCCTTCT, SEQ ID NO: 1, reverse primer: ggatccGGCGGCAGCTGTTGTTGATGT), SEQ ID NO: 2, and a 2448 downstream fragment (forward primer: agatctAAATAATGTACTAGAGACACT, SEQ ID NO: 3, reverse primer: ctcgagTTCCACCAACACTCCAGAGTG) SEQ ID NO: 4, (Restriction sites added for cloning purposes are shown in lower case.) These fragments were cloned in the pDE3 plasmid in the SalI and XhoI sites of the plasmid, using the BamHI/BglII ligation compatibility. The SfiI/BamHI fragment from this plasmid was subcloned into pSL1190 plasmid (Pharmacia) and sequenced. It was subsequently cloned into pDE3-ext plasmid in the same sites, generating pDE3-ext-ΔPS plasmid. To generate protease-deleted Ad mutants, recombination into *E. coli* was chosen (FIG. 3). An E1/E3 deleted mutant: Ad5CMVLacZ-CMVGFP-ΔPS was constructed in plasmid by cotransfection in *E. coli* of the NdeI/XhoI fragment from pDE3-ext-ΔPS with pAdEasy1-βgal-GFP SgfI digested. A mutant deleted only for the protease (Ad5-ΔPS) was generated in the same manner from pTG3602 plasmid. Seven micrograms of plasmid DNA PacI digested from both pAdEasy1-βgal-GFP and pTG3602-ΔPS were transfected in 293-PS-rtTA-7 cell line clone to generate recombinant protease-deleted mutants. The same amount of recombinant linearized plasmid DNAs were also transfected in 293 and 293-rtTA cells as controls. As expected, this experiment yielded no viral plaques. After 10–14 days viral plaques were observed in 293-PS-rtTA. As recombinant adenoviruses have been generated in *E.coli*, no further cloning of plaques was required (He et al, 1998; Chartier et al, 1996). The whole monolayer was scraped and virus was released from cells by freeze-thaw cycles. All viral plaques of recombinant virus displayed no phenotypic differences from that of wild-type virus.

Ability of Ad5-ΔPS Mutant not Deleted for E1 to Perform a Single Round of Replication in Non-Complementing Cell Lines.

Figure 6:
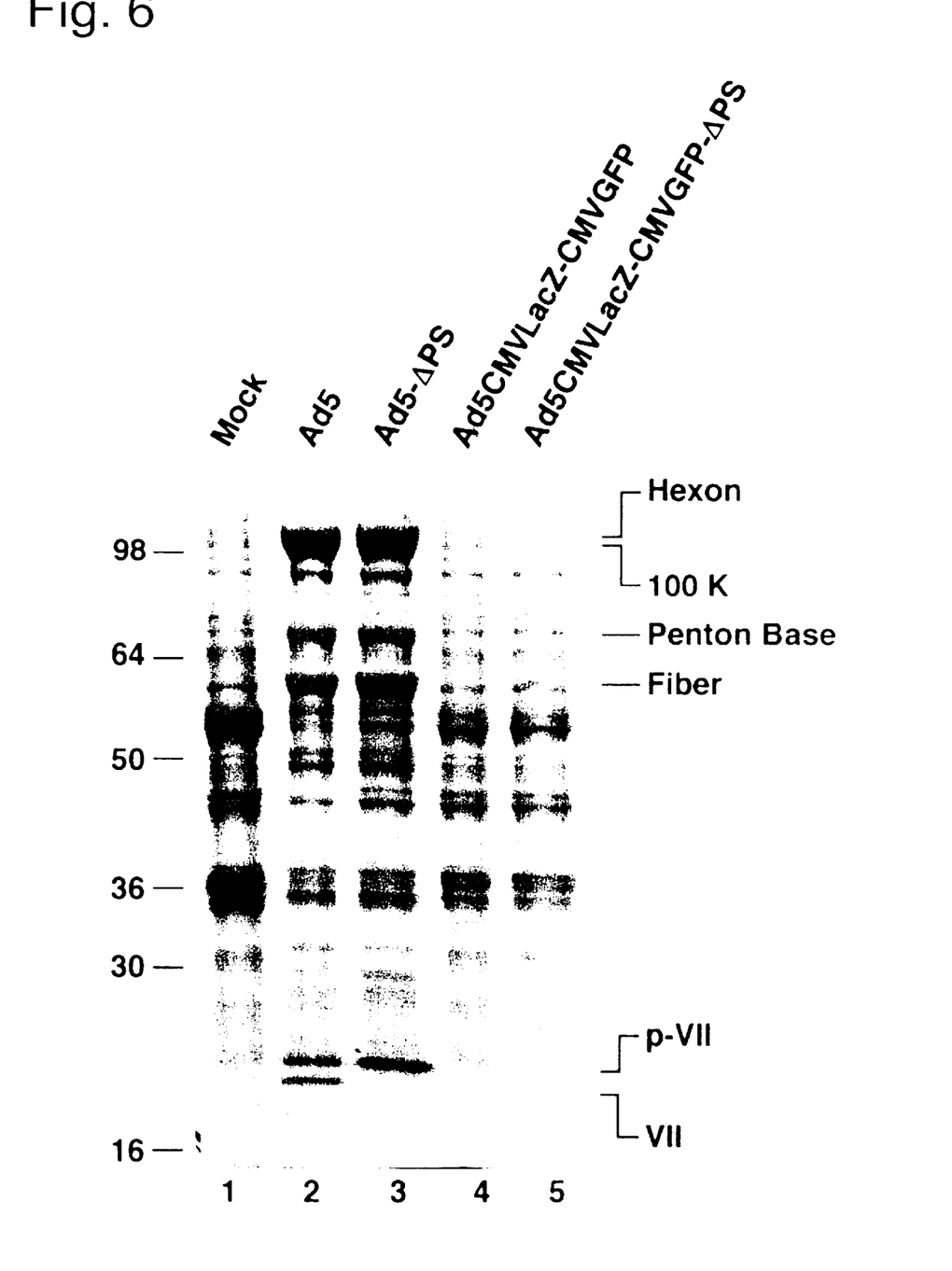
FIG. 6 is a photograph showing a Coomassie blue stained gel demonstrating the ability of Ad5-ΔPS mutant to perform a single round of replication in non-complementing cells. A549 cells were inoculated at a MOI of 5 pfu with indicated mutants. 3 days later the cells were lysed in Laemmli buffer. 20 micrograms of protein extracts were loaded per well and migrated in a 12% acrylamide:bisacrylamide gel. Comparison of viral protein synthesized by the different mutants (i.e. hexon, 100K) shows that only Ad5-ΔPS mutant produces them in amounts similar to that of wild-type virus. This confirms the ability of this mutant to perform a single round of replication in non-complementing cells.
Figure 7:
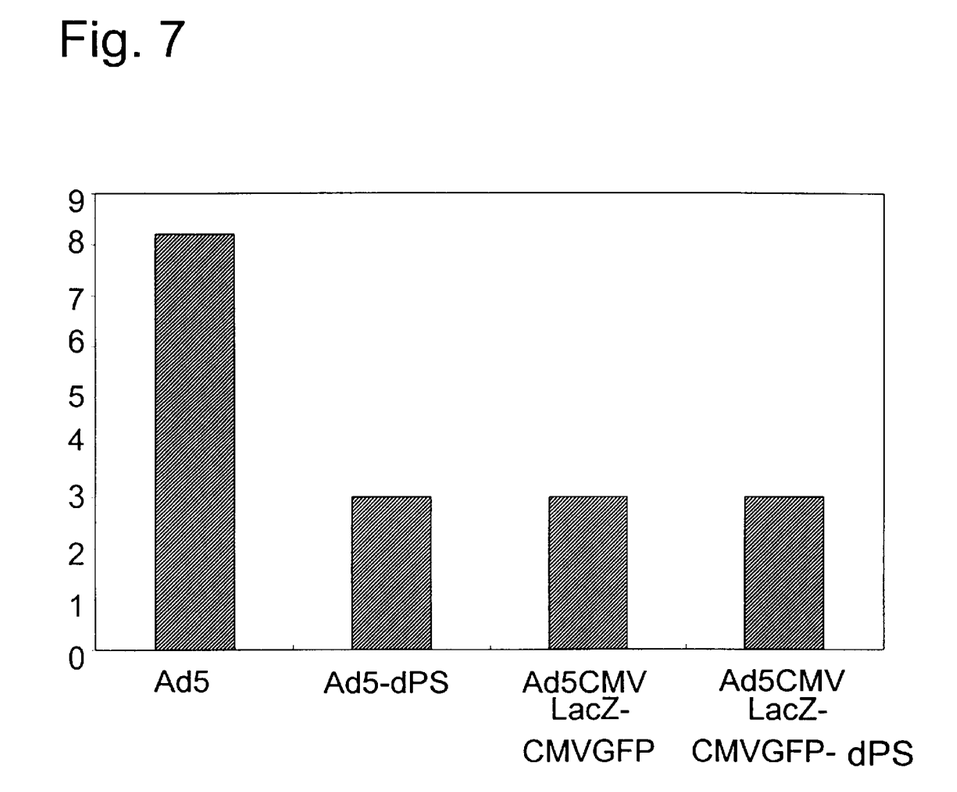
FIG. 7 is a graph showing the viral yields of different adenoviral mutants in A549 cells. The ability of Ad5-ΔPS mutant to perform a single round of replication in non-complementing cells was further determined by titration of the same extracts as presented in FIG. 6. A549 cells were inoculated at a MOI of 5 pfu with indicated mutants. 3 days later, cells were harvested and extracts were titrated in 293rtTA.PS.7. Titers are indicated in log values (0–9).

To demonstrate the ability of the mutant deleted for the protease and not for E1 (Ad5-ΔPS) to perform a single round of replication in non-complementing cell lines, A549 cells were inoculated with wild-type, Ad5-ΔPS, AdΔE1.E3, and Ad5CMVLacZ-CMVGFP-ΔPS viruses. Comparison of viral protein production (FIG. 6) and of viral yields (FIG. 7) of the different viruses show that only the mutant deleted for the protease and not for E1 is able of undergoing a single round of replication in non-complementing cells.

The following cell line was deposited under the Budapest Treaty with the American Type Culture Collection (ATCC), 10801 University Boulevard, Manassas, Va. 20110-2209, on Nov. 17, 1998, and assigned the following accession number: 293 rtTA.PS.7 cell line: ATCC CRL 12595

Although various particular embodiments of the present invention have been described herein before, for purposes of illustration, it would be apparent to those skilled in the art that numerous variations may be made thereto without departing from the spirit and scope of the invention, as defined in the appended claims.

---

What is claimed is:

1. A cell line capable of hosting and complementing in trans an adenovirus deleted for the gene of adenovirus protease, said cell line containing adenovirus DNA recombinantly expressing the adenovirus protease, said adenovirus DNA consisting essentially of DNA that encodes the adenovirus protease.

2. The cell line according to claim 1, wherein said DNA expressing the adenoviral protease is expressed from an expression cassette comprising a regulatable promoter.

3. The cell line according to claim 2, wherein said regulatable promoter is a tetracycline derivative responsive promoter.

4. The cell line according to claim 3, wherein said tetracycline derivative responsive promoter is an inducible promoter.

5. The cell line according to claim 4, wherein said tetracycline derivative inducible promoter is the rtTA-dependent minimal promoter.

6. The cell line according to claim 3, wherein said tetracycline derivative responsive promoter is a repressible promoter.

7. The cell line according to claim 6, wherein said tetracycline derivative repressible promoter is the tTA-dependent minimal promoter.

8. The cell line according to claim 2, wherein said expression cassette further comprises DNA encoding a fluorescent protein.

9. The cell line according to claim 8, wherein said expression cassette is a dicistronic expression cassette.

10. The cell line according to claim 8, wherein said fluorescent protein is the *Aquorea victoria* green fluorescent protein (GEP).

11. The cell line according to claim 1, wherein said coils are mammalian cells.

12. The cell line according to claim 11, wherein said mammalian cells are human cells.

13. The cell line according to claim 12, wherein said human cells are 293 cell line derivatives.

14. The cell line according to claim 13, deposited with the ATCC and assigned accession number ATCC CRL-12595.

15. A method of producing a cell line capable of hosting and complementing in trans an adenovirus deleted for the gene of adenovirus protease, said cell line containing adednovirus DNA recombinantly expressing the adenovirus protease, said adenovirus DNA consisting essentially of DNA that encodes the adenovirus protease, said method comprising:

transfecting cells capable of hosting an adenovirus with pieces of DNA encoding the adenovirus protease,
incubating said cells, and
selecting cells expressing the adenovirus protease.

16. The method of claim 15, wherein said cells capable of hosting an adenovirus deleted for the gene of adenovirus protease are derivatives of 293 cells.

17. The method according to claim 15, wherein said pieces of DNA encoding adenoviral protease are contained within a plasmid.

18. The method according to claim 17, wherein said plasmid is pTR5/PS-DC/GFP plasmid.

19. The method according to claim 15, further comprising cotransfecting said pieces of DNA encoding the adenoviral protease with pieces of DNA encoding a selection factor, and selecting cells expressing said selection factor.

20. The method according to claim 19, wherein said pieces of DNA encoding a selection factor are contained within a plasmid.

21. The method according to claim 20, wherein said DNA encoding a selection factor is the gene of resistance to geneticin (G418 antibiotic).

22. The method according to claim 20, wherein said plasmid is pTKNeo plasmid.

23. The method according to claim 20, wherein said DNA encoding a selection factor is the gene of resistance to hygromycin.

24. The method according to claim 20, wherein said plasmid is p3'SS plasmid.

25. The method according to claim 19, wherein said pieces of DNA encoding the adenovirus protease and said pieces of DNA encoding a selection factor are cotransfected by the calcium phosphate precipitation method.

26. The method according to claim 15, wherein said pieces of DNA encoding the adenovirus protease further comprise a reporter gene.

27. The method according to claim 26, wherein said reporter gene is the gene of a fluorescent protein.

28. The method according to claim 27, wherein said fluorescent protein is the *Aquorea victoria* green fluorescent protein (GFP).

29. The method according to claim 28, wherein cells expressing said OFF reporter gene are selected by automated fluorescent cell sorting.

* * * * *